United States Patent [19]
Schell et al.

[11] Patent Number: 5,583,612
[45] Date of Patent: Dec. 10, 1996

[54] FLEXIBLE LATCH WITH RELAXED ENGAGEMENT

[75] Inventors: Richard P. Schell, Webster; Brian E. Gangloff; Bruce C. Reynolds, both of Rochester, all of N.Y.

[73] Assignee: Xerox Corporation, Stamford, Conn.

[21] Appl. No.: 275,180

[22] Filed: Jul. 14, 1994

[51] Int. Cl.$^6$ .................................................. G03G 15/00
[52] U.S. Cl. ............................................ 355/200; 292/80
[58] Field of Search ................................ 355/200, 210, 355/211; 292/80, 87, 219, DIG. 38; 347/152

[56] References Cited

U.S. PATENT DOCUMENTS

| | | | |
|---|---|---|---|
| 1,744,960 | 1/1930 | Garbell | 292/80 X |
| 4,156,311 | 5/1979 | Wallace et al. | 30/262 |
| 4,534,586 | 8/1985 | Smith | 292/DIG. 38 X |
| 4,831,777 | 5/1989 | Johnson, Jr. | 49/55 |
| 5,066,976 | 11/1991 | Kanagawa et al. | 355/200 |
| 5,151,051 | 9/1992 | Nagamine | 439/557 |
| 5,248,264 | 9/1993 | Long et al. | 439/347 |
| 5,261,557 | 11/1993 | Bytell et al. | 220/662 |

FOREIGN PATENT DOCUMENTS 1781476  9/1979  Germany ...................... 292/DIG. 38

*Primary Examiner*—Shuk Yin Lee
*Attorney, Agent, or Firm*—John S. Wagley

[57] ABSTRACT

A latch for releasably securing a member to a support structure. The latch includes a substantially rigid member mounted pivotably in the member. The rigid member includes a catch disposed at one end thereof and a handle at another end thereof. The rigid member also includes a substantially resilient member coupled to the rigid member for urging the rigid member to pivot to a position in which the catch thereof engages the support structure to secure the member thereto. The handle is adapted to pivot the rigid member to release the catch from engagement with the support structure to release the member.

15 Claims, 4 Drawing Sheets

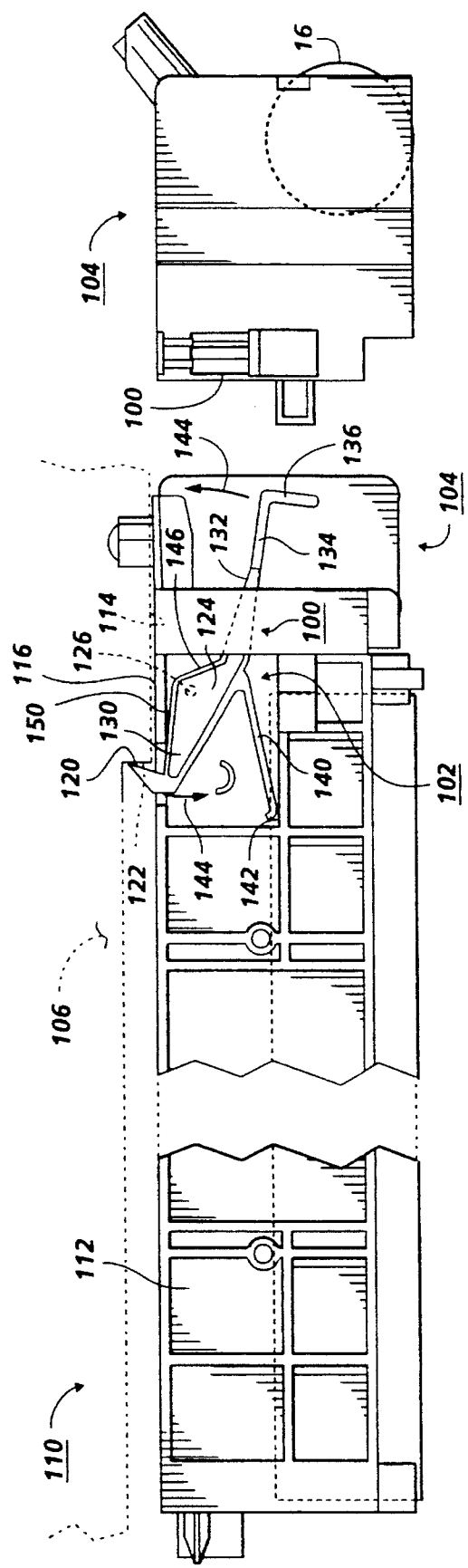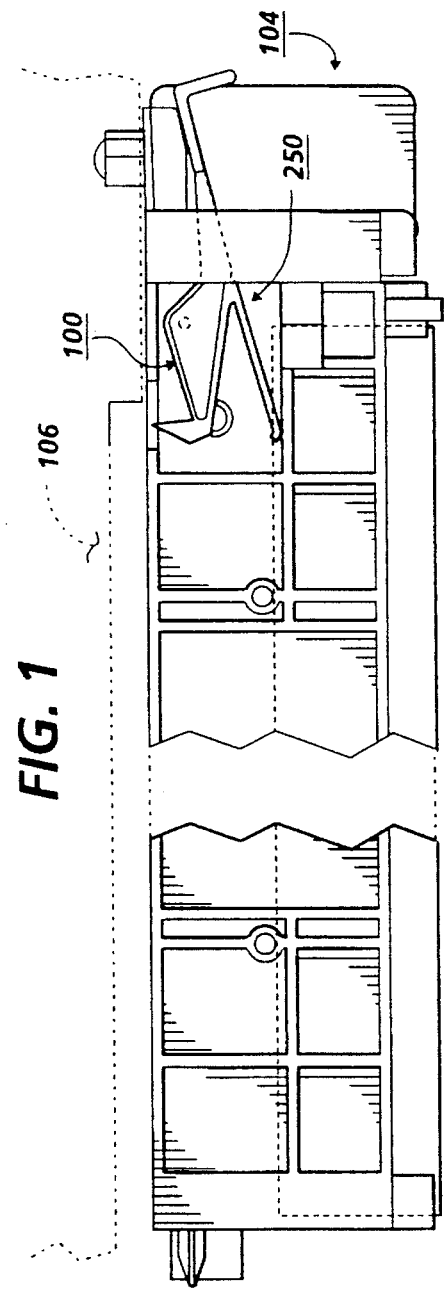
FIG. 1  FIG. 2  FIG. 5

FLEXIBLE LATCH WITH RELAXED ENGAGEMENT

The present invention relates to a method and apparatus for latching a sliding member in place. More specifically, the invention relates to a flexible latch.

Latches are frequently used to temporarily secure devices constrained to move in a certain path. Typically latches include a catch that rotates about a pivot point and a spring that biases the latch in a direction to secure the catch against a stop in the device. Such devices include a plurality of components including at least the latch and the spring. Often the devices include a separate pivot pin and retainers to secure the pivot pin and the spring to the latch. Each of the components must be assembled onto the latch to provide the latch assembly. Such devices are expensive to manufacture and assemble.

Since the electrophotographic printing machine includes many subassemblies that slide along tracks or rotate around pivot points to ease assembly and subsequent servicing of the unit, the features of the present invention are useful in the printing arts and more particularly in electrophotographic printing. In particular, the customer replaceable unit CRU is frequently serviced during the life of the copy machine, and as such is typically mounted on tracks for easy servicing. The CRU typically slides along a track and is secured axially in the track of the copy machine by a latch.

In the well-known process of electrophotographic printing, the charge retentive surface, typically known as a photoreceptor, is electrostatically charged, and then exposed to a light pattern of an original image to selectively discharge the surface in accordance therewith. The resulting pattern of charged and discharged areas on the photoreceptor form an electrostatic charge pattern, known as a latent image, conforming to the original image. The latent image is developed by contacting it with a finely divided electrostatically attractable powder known as "toner." Toner is held on the image areas by the electrostatic charge on the photoreceptor surface. Thus, a toner image is produced in conformity with a light image of the original being reproduced. The toner image may then be transferred to a substrate or support member (e.g., paper), and the image affixed thereto to form a permanent record of the image to be reproduced. Subsequent to development, excess toner left on the charge retentive surface is cleaned from the surface. The process is useful for light lens copying from an original or printing electronically generated or stored originals such as with a raster output scanner (ROS), where a charged surface may be imagewise discharged in a variety of ways.

The following disclosures may be relevant to various aspects of the present invention:

U.S. Pat. No. 5,261,557
Patentee: Bytell et al.
Issue Date: Nov. 16, 1993
U.S. Pat. No. 5,248,264
Patentee: Long et al.
Issue Date: Sep. 28, 1993
U.S. Pat. No. 5,151,051
Patentee: Nagamine
Issue Date: Sep. 29, 1992
U.S. Pat. No. 4,831,777
Patentee: Johnson, Jr.
Issue Date: May 23, 1989
U.S. Pat. No. 4,156,311
Patentee: Wallace et al.
Issue Date: May 29, 1979

U.S. Pat. No. 5,261,557 discloses a decorative window for use with a sanitary product dispenser. A decorative strip support releasably engages the window from within the dispenser. The strip support includes a flexible latch that is engageable with the window. A latch bolt located near the end of a flexible latch bar on a support member cooperates with a latch bolt opening in the window to removably latch the window to the support member.

U.S. Pat. No. 5,248,264 discloses a carrier for receiving a portable product. The portable product includes a protruding member. The carrier includes a latch assembly that cooperates with the protruding member. A flexible member supports the latch assembly allowing flexing in a direction transverse to the latch assembly. A spring biases the latch assembly into a locked position. A ramp on the latch assembly cooperates with the protruding member to open the latch.

U.S. Pat. No. 5,151,051 discloses a panel mounted electrical connector including a plastic housing with flexible latches. The flexible latches swing about an internal hinge portion. The latches are driven inwardly as the connector is forced into an aperture in a panel and spring outwardly to engage the edge of the panel to engage the connector. The latch has a recess at the internal hinge portion to prevent over stressing of the hinge.

U.S. Pat. No. 4,831,777 discloses a latch for a safety gate. The latch pivots about a pivot point which has a pin which is secured by an anchor screw. Teeth on one end of the latch mate with teeth on a rack to provide width adjustment for the gate. A flange on the other end of the latch mates with a recess in the gate to spring the flange to bias the teeth on the latch into interference with the rack.

U.S. Pat. No. 4,156,311 discloses a latch for a hand shear. The latch includes a flexible plastic stud that slidably fits into a slot in one handle of the shears with one end of the stud outboard to be engageable by the operator and the other end inboard to provide interference with a lock stud in both a locked open position and a locked closed position. The plastic stud has ears that interferencely fit through the slot in the handle to lock it thereto.

SUMMARY OF THE INVENTION

In accordance with one aspect of the present invention, there is provided a latch for releasably securing a member to a support structure. The latch includes a substantially rigid member mounted pivotably in the member. The rigid member includes a catch disposed at one end thereof and a handle at another end thereof. The rigid member also includes a substantially resilient member coupled to the rigid member for urging the rigid member to pivot to a position in which the catch thereof engages the support structure to secure the member thereto. The handle is adapted to pivot the rigid member to release the catch from engagement with the support structure to release the member.

In accordance with another aspect of the present invention, there is provided a customer replaceable unit including a processing station for use in a printing machine. The customer replaceable unit includes a latch for releasably securing the customer replaceable unit to the printing machine. The latch includes a substantially rigid member mounted pivotably in the member. The rigid member includes a catch disposed at one end thereof and a handle at another end thereof. The rigid member also includes a substantially resilient member coupled to the rigid member for urging the rigid member to pivot to a position in which the catch thereof engages the support structure to secure the member thereto. The handle is adapted to pivot the rigid member to release the catch from engagement with the support structure to release the member.

In accordance with yet another aspect of the present invention, there is provided an electrophotographic printing machine of the type including a customer replaceable unit having a processing station therein. The printing machine includes a latch for releasably securing the customer replaceable unit to the printing machine. The latch includes a substantially rigid member mounted pivotably in the member. The rigid member includes a catch disposed at one end thereof and a handle at another end thereof. The rigid member also includes a substantially resilient member coupled to the rigid member for urging the rigid member to pivot to a position in which the catch thereof engages the support structure to secure the member thereto. The handle is adapted to pivot the rigid member to release the catch from engagement with the support structure to release the member.

BRIEF DESCRIPTION OF THE DRAWINGS

The invention will be described in detail herein with reference to the following figures in which like reference numerals denote like elements and wherein:

FIG. 1 is an elevational view of an embodiment of the integral flexible latch of the present invention installed onto a customer replaceable unit of an electrophotographic copy machine with the latch in the relaxed position;

FIG. 2 is an end elevational view of the integral flexible latch of FIG. 1;

FIG. 5 is an elevational view of the integral flexible latch of FIG. 1 installed onto the customer replaceable unit with the latch in the strained position.

While the present invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

Figure 6:
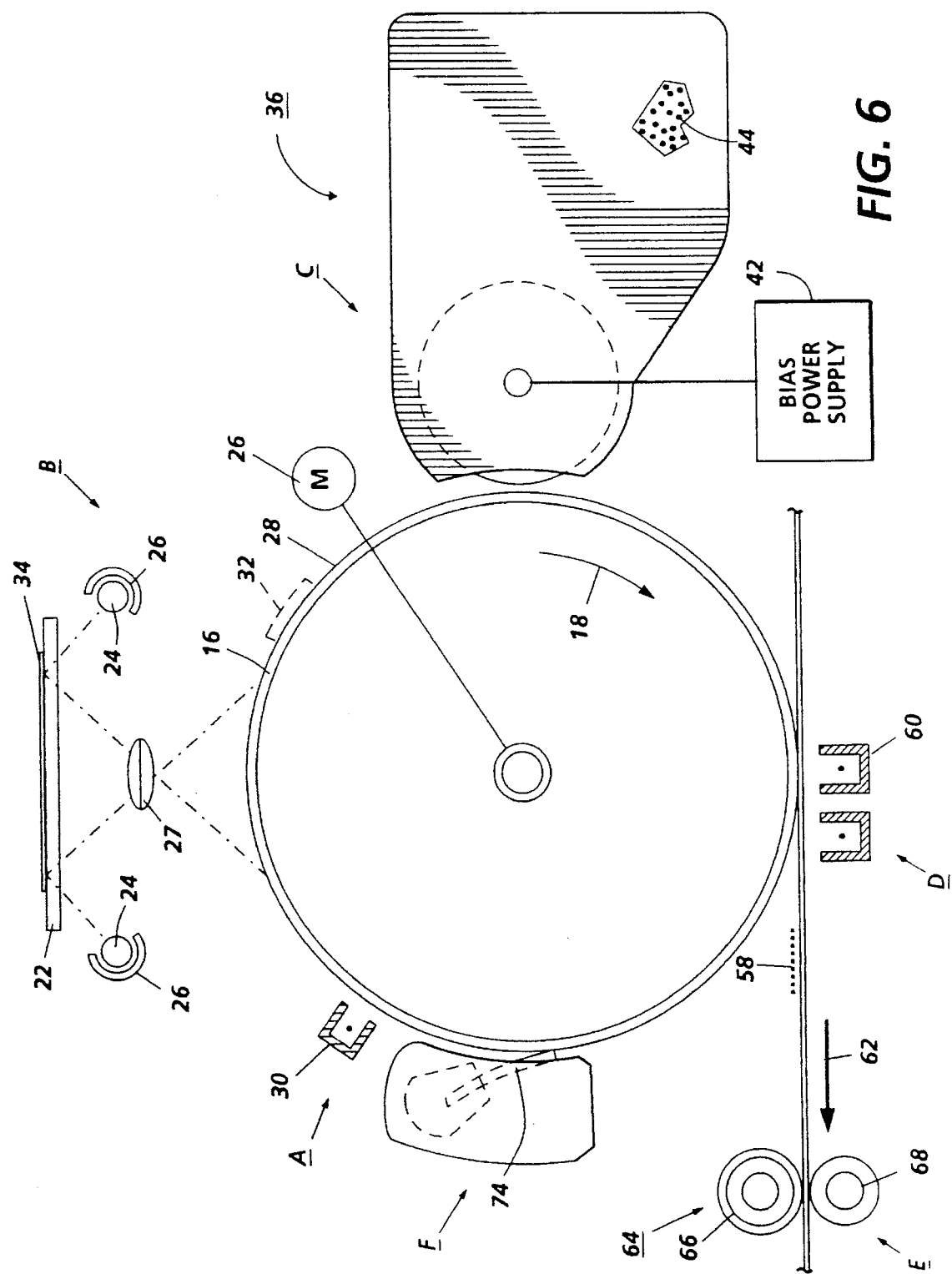
FIG. 6 is a schematic elevational view of an illustrative electrophotographic printing machine incorporating the integral flexible latch of the present invention therein.

For a general understanding of the illustrative electrophotographic printing machine incorporating the features of the present invention therein, reference is made to the drawings. In the drawings, like reference numerals have been used throughout to designate identical elements. FIG. 6 schematically depicts the various components of an electrophotographic printing machine incorporating the integral flexible latch of the present invention therein. Although the integral flexible latch of the present invention is particularly well adapted for use in the illustrative printing machine, it will become evident that the integral flexible latch is equally well suited for use in a wide variety of machines where sliding or pivoting members are secured and are not necessarily limited in their application to the particular embodiments shown herein.

Referring now to FIG. 6, the electrophotographic printing machine shown employs a photoconductive drum 16, although photoreceptors in the form of a belt are also known, and may be substituted therefor. The drum 16 has a photoconductive surface deposited on a conductive substrate. Drum 16 moves in the direction of arrow 18 to advance successive portions thereof sequentially through the various processing stations disposed about the path of movement thereof. Motor 26 rotates drum 16 to advance drum 16 in the direction of arrow 18. Drum 16 is coupled to motor 26, by suitable means such as a drive.

Initially successive portions of drum 16 pass through charging station A. At charging station A, a corona generating device, indicated generally by the reference numeral 30, charges the drum 16 to a selectively high uniform electrical potential. The electrical potential is normally opposite in sign to the charge of the toner. Depending on the toner chemical composition, the potential may be positive or negative. Any suitable control, well known in the art, may be employed for controlling the corona generating device 30.

A document 34 to be reproduced is placed on a platen 22, located at imaging station B, where it is illuminated in a known manner by a light source such as a lamp 24 with a photo spectral output matching the photo spectral sensitivity of the photoconductor. The document thus exposed is imaged onto the drum 16 by a system of mirrors 26 and lens 27, as shown. The optical image selectively discharges surface 28 of the drum 16 in an image configuration whereby an electrostatic latent image 32 of the original document is recorded on the drum 16 at the imaging station B At development station C, a development system or unit, indicated generally by the reference numeral 36 advances developer materials into contact with the electrostatic latent images. The developer unit includes a device to advance developer material into contact with the latent image.

The developer unit 36, in the direction of movement of drum 16 as indicated by arrow 18, develops the charged image areas of the photoconductive surface. This developer unit contains, for example, black developer material 44 having a triboelectric charge such that the black toner is attracted to charged areas of the latent image by the electrostatic field existing between the photoconductive surface and the electrically biased developer rolls in the developer unit, which are connected to the bias power supply 42, attracts the toner to the latent image.

A sheet of support material 58 is moved into contact with the toner image at transfer station D. The sheet of support material 58 is advanced to transfer station D by conventional sheet feeding apparatus, not shown. Preferably, the sheet feeding apparatus includes a feed roll contacting the uppermost sheet of a stack of copy sheets. Feed rolls rotate so as to advance the uppermost sheet from the stack into a chute which directs the advancing sheet of support material into contact with the photoconductive surface of drum 16 in a timed sequence so that the toner powder image developed thereon contacts the advancing sheet of support material at transfer station D.

Transfer station D includes a corona generating device 60 which sprays ions of a suitable polarity onto the backside of sheet 58. This attracts the toner powder image from the drum 16 to sheet 58. After transfer, the sheet continues to move, in the direction of arrow 62, onto a conveyor (not shown) which advances the sheet to fusing station E.

Fusing station E includes a fuser assembly, indicated generally by the reference numeral 64, which permanently affixes the transferred powder image to sheet 58. Preferably, fuser assembly 64 comprises a heated fuser roller 66 and a pressure roller 68. Sheet 58 passes between fuser roller 66 and pressure roller 68 with the toner powder image contacting fuser roller 66. In this manner, the toner powder image is permanently affixed to sheet 58. After fusing, a chute, not shown, guides the advancing sheet 58 to a catch tray, also not shown, for subsequent removal from the printing machine by the operator. It will also be understood that other post-fusing operations can be included, for example, binding, inverting and returning the sheet for duplexing and the like.

After the sheet of support material is separated from the photoconductive surface of drum 16, the residual toner particles carried by image and the non-image areas on the photoconductive surface are removed at cleaning station F. The cleaning station F includes a blade 74.

It is believed that the foregoing description is sufficient for purposes of the present application to illustrate the general operation of an electrophotographic printing machine incorporating the development apparatus of the present invention therein.

According to the present invention, and referring to FIG. 1, an integral flexible latch 100 is shown in a first relaxed position 102 in a customer replaceable unit 104 installed within a support structure 106 in a copy machine or printing machine 110.

The customer replaceable unit 104 includes a housing or cartridge 112 to which several components, namely those components found to require replacement on a more frequent basis within the copy machine 110 are mounted. Typically, the customer replaceable unit 104 includes the photoreceptive drum 16 (see FIG. 6) and other items determined to wear at a significant rate. For example, the customer replaceable unit 104 may include the blade 74 of the cleaning station F and the corona generating device 30 of the charging station A (see FIG. 6).

To aid in the easy servicing of the copy machine 110, the customer replaceable unit 104 is typically designed to be easily removed from the copy machine 110. A typical arrangement for the ease of replacement of the customer replaceable unit 104 includes having the support structure 106 of the copy machine 110 includes rails 114 which guide outer faces 116 of the customer replaceable unit 104.

To restrain the customer replaceable unit 104 within the rails 114 of the support structure 106 of the copy machine 110, the latch 100 is provided to secure the customer replaceable unit 104 therein. Latch 100 includes a catch 120, preferably in the form of a wedge shaped lip which is contactable with a shoulder 122 of the support structure 106 of the copy machine 110 adjacent the rails 114.

The latch 100 includes a rigid member 124 which is preferably pivotable about a pivot pin 126. The rigid member 124 includes a first arm 130 to which the lip 120 is distally located. The rigid member 124 also includes a second arm 132 which extends from the pin 126 outwardly. The second arm 132 serves as a release or lever to permit rotation of the rigid member 124 about the pin 126 in order to rotate the first arm 130 and the lip 120 which is located therein both into and away from the shoulder 122 to which it interacts. Preferably, located distally on the second arm 132 is a handle 134 which serves to provide ability to rotate the second arm 132. The handle 134 also serves to move the rigid member 124 and, correspondingly, the customer replaceable unit 104, laterally along the rails 114 of the support structure 106. To assist in the lateral translation of the customer replaceable unit 104, the handle 134 preferably includes a handle lip 136 located on the end of the handle 134.

The latch 100 also includes a resilient member 140 which extends outwardly from the rigid member 124. The resilient member 140 is in contact on its distal end thereof with a stop 142 on the customer replaceable unit 104. The resilient member 140 may have any suitable shape and be made from any suitable material that is resilient. The resilient member 140 may be, for example, in the form of a leaf spring or alternatively may be in the form of a coil spring. The resilient member 140 as shown in FIG. 1 is in the form of an arm or leaf spring. The leaf spring 140 is in a relaxed position as shown in FIG. 1. Rotation of the latch 100 in the direction of arrows 144 causes the leaf spring 140 to become strained and urge the latch 100 back into the position as shown in FIG. 1. To minimize manufacturing and assembly costs, the resilient member 140 is integral with the rigid member 124. The latch 100 therefore needs to be made of a material that exhibits rigid properties with a larger cross section such as that shown in the rigid member 124 yet remains resilient when in a smaller cross section such as that of the resilient member 140 of FIG. 1. Suitable materials include but are not limited to metals and synthetics. Synthetic materials such as polycarbonate or acetal are particularly conducive to a latch 100 as disclosed by the inventors.

The cross section of the rigid member 124 as earlier mentioned is significantly larger than the cross section of the resilient member 140. The rigid member 124 may have a uniform cross section or, as shown in FIG. 1, may include ribs 146 to provide a larger cross section along periphery 150 of the rigid member 124 in order to enhance the rigidity of the rigid member 124.

Figure 3:
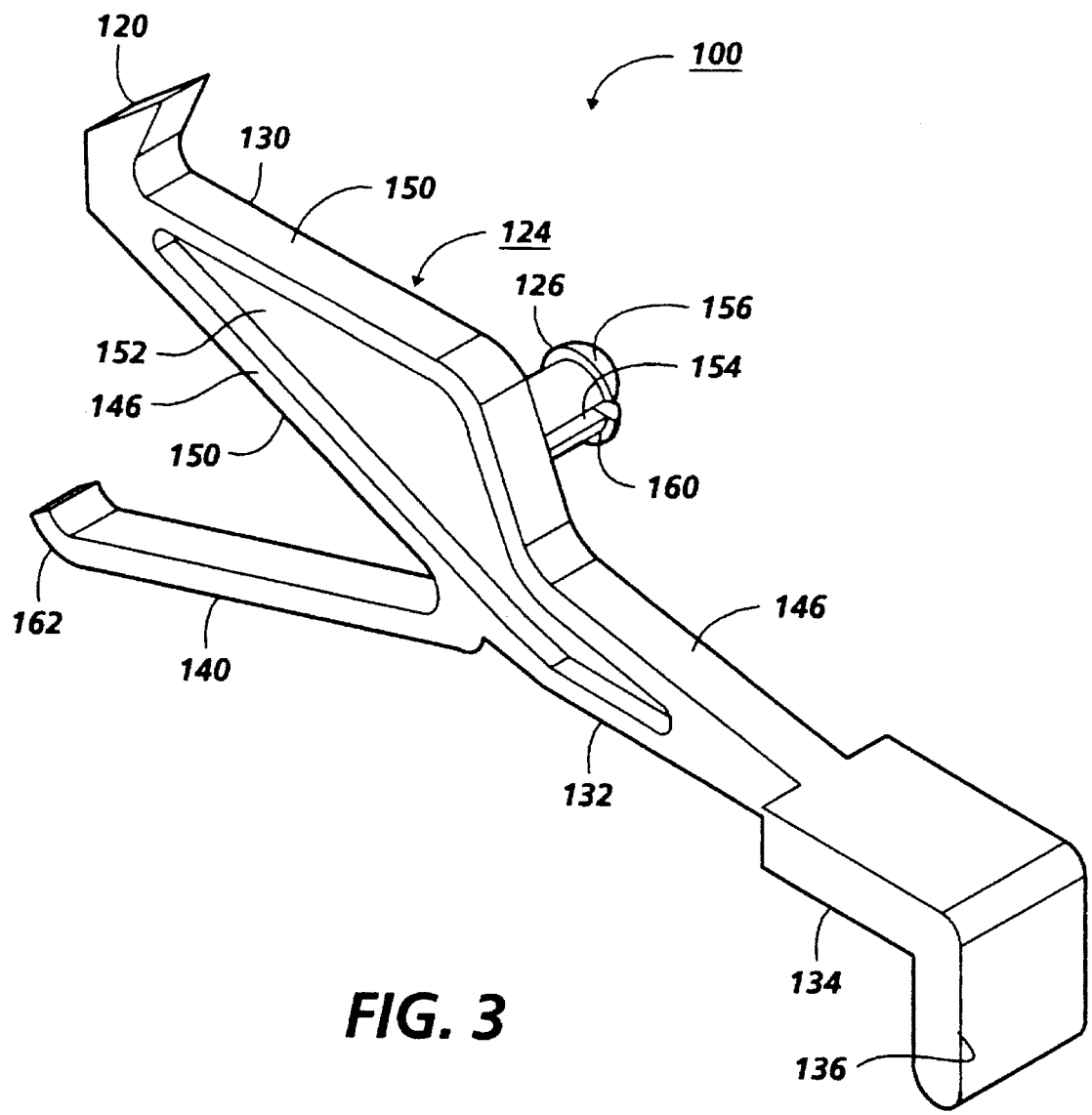
FIG. 3 is a perspective view of the integral flexible latch of FIG. 1.

Referring to FIG. 3, the latch 100 is shown in its relaxed position in greater detail. The first arm 130 and the second arm 132 include a thin body 152 which is surrounded by the ribs 146 which provides a larger cross section for the periphery 150 than that for the body 152 of the arms 130 and 132. The ribs 146 are substantially thicker than the body 152 providing the rigidity desirable for the rigid member 124 yet allowing the resilient member 140 to be made from a homogeneous material and yet be flexible.

The pin 126 about which the latch 100 rotates may have any suitable form and is also preferably integral with the rigid member 124 and the resilient member 140. Preferably, the pin 126 is in the form of a stud which extends perpendicularly to the rigid member 124. The pin 126 has a generally cylindrical shape with a slit 154 extending centrally therethrough to provide for the contraction of the pin 126 during assembly into a mating opening (not shown) in the customer replaceable unit 104. The pin 126 also includes a dome-shaped knob 156 which extends peripherally beyond the distal end of the cylindrical portion of the pin 126 and includes a shoulder 160 between the dome shape knob 156 and the cylindrical portion of the pin 126. The shoulder 160 of the pin 126 serves to restrain the pin 126 within the mating opening of the customer replaceable unit 104.

The resilient member 140 may include an arcuate portion 162 at the end thereof to provide for an improved contact with the stop 142 of the customer replaceable unit 104 (see FIG. 1).

Figure 4:
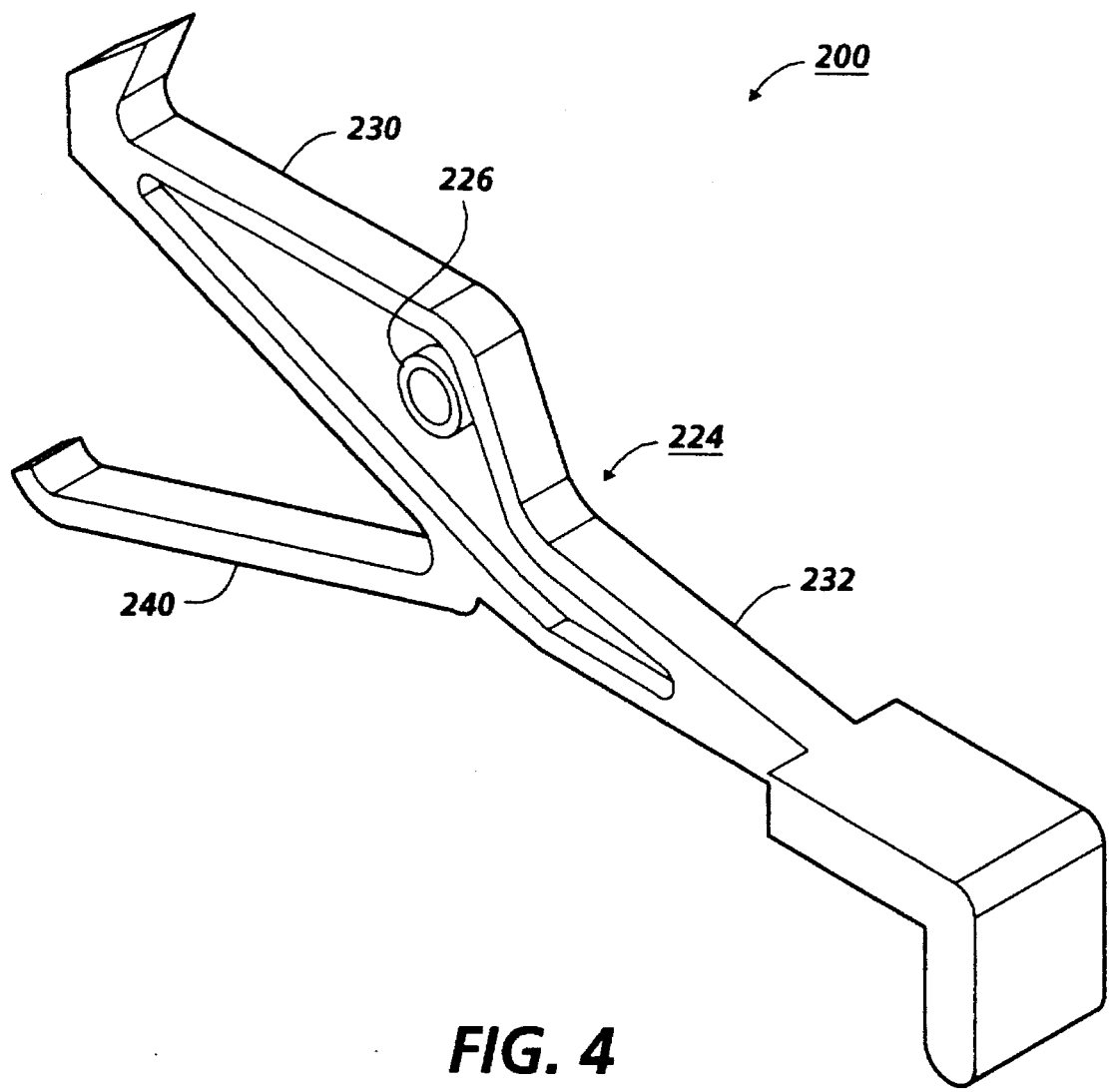
FIG. 4 is a perspective view of an alternate embodiment of the integral flexible latch of the present invention including a pivoting hole.

While the pin 126 of the latch 100 of FIG. 3 may provide preferable pivoting of the latch 100, the pivoting of a latch of the present invention may be provided with alternate configurations such as that of FIG. 4. Latch 200 includes first and second arms 230 and 232, respectively, extending therefrom which arms 230 and 232 form a rigid member 224. A resilient member 240 extends from the rigid member 224. An opening in the form of a bore 226 provides for the rotation of the latch 200. A stud (not shown) similar to the pin 126 of FIG. 3 is an integral part of the customer replaceable unit (not shown) to which the latch 200 interacts.

Since the latch of the present invention is preferably made of a synthetic material having resilient properties, such as polycarbonate or acetal, and since materials such as polycarbonate or acetal have a tendency to creep and/or fatigue when placed in a strained position for an extended period of time, the latch 100 as shown in FIG. 1 is in a relaxed position when the catch 120 interacts with the shoulder 122 of the support structure 106. Referring to FIG. 5, the latch 100 is in a restrained position 250 only when the customer replaceable unit 104 needs to be removed from the support structure 106. The restrained position 250 as shown in FIG. 5 represents a very small portion of the service life of the customer replaceable unit 104, while the first relaxed position 102 as shown in FIG. 1 represents the vast majority of service life of the customer replaceable unit 104.

The integral molded plastic latch of the present invention provides for an inexpensive durable latch that may be quickly and easily assembled with no required tooling and inexpensively manufactured from inexpensive materials.

The resilient member being integral with the rigid member provides for an inexpensive moldable one piece construction of an inherently retractable latch.

The relaxed when latched configuration of the latch of the present invention provides for a long service life.

While this invention has been described in conjunction with various embodiments, it is evident that many alternatives, modifications, and variations will be apparent to those skilled in the art. Accordingly, it is intended to embrace all such alternatives, modifications, and variations as fall within the spirit and broad scope of the appended claims.

What is claimed is:

1. A latch for releasably securing a first member to a support structure, comprising:

a substantially rigid member mounted pivotably in the first member, said rigid member including a catch disposed at one end thereof and a handle at another end thereof; and a substantially resilient member coupled to said rigid member for urging said rigid member to pivot to a first position in which the catch thereof engages the support structure to secure the first member thereto, said resilient member being in a relaxed position when said rigid member is in the first position, and a second position in which the catch thereof does not engage the support structure, said resilient member being in a restrained position when said rigid member is in the second position, said handle pivoting with said rigid member to release the catch from engagement with the support structure to release the first member.

2. A latch according to claim 1, wherein said resilient member comprises a leaf spring.

3. A latch according to claim 1, wherein said rigid member comprises a pin intermediate the catch and the handle for pivotably attaching said rigid member to the first member.

4. A latch according to claim 1, wherein the catch of said rigid member comprises a wedge shaped lip.

5. A latch according to claim 2, wherein said leaf spring has one end thereof attached to said rigid member intermediate the catch and the handle with the other end thereof being free.

6. A customer replaceable unit including a processing station for use in a printing machine comprising:

a latch for releasably securing the customer replaceable unit to the printing machine, said latch comprising a substantially rigid member mounted pivotably in the customer replaceable unit, said rigid member including a catch disposed at one end thereof and a handle at another end thereof, and a substantially resilient member coupled to said rigid member for urging said rigid member to pivot to a first position in which the catch thereof engages the printing machine to secure the customer replaceable unit thereto, said resilient member being in a relaxed position when said rigid member is in the first position, and a second position in which the catch thereof does not engage the printing machine, said resilient member being in a restrained position when said rigid member is in the second position, said handle pivoting with said rigid member to release the catch from engagement with the printing machine to release the customer replaceable unit.

7. A customer replaceable unit according to claim 6, wherein said resilient member comprises a leaf spring.

8. A customer replaceable unit according to claim 6, wherein said rigid member comprises a pin intermediate the catch and the handle for pivotably attaching said rigid member to the customer replaceable unit.

9. A customer replaceable unit according to claim 6, wherein the catch comprises a wedge shaped lip.

10. A customer replaceable unit according to claim 7, wherein said leaf spring has one end thereof attached to said rigid member intermediate the catch and the handle with the other end thereof being free.

11. An electrophotographic printing machine of the type including a customer replaceable unit having a processing station therein, comprising:

a latch for releasably securing the customer replaceable unit to the printing machine, said latch comprising a substantially rigid member mounted pivotably in the customer replaceable unit, said rigid member including a catch disposed at one end thereof and a handle at another end thereof, and a substantially resilient member coupled to said rigid member for urging said rigid member to pivot to a first position in which the catch thereof engages the printing machine to secure the customer replaceable unit thereto, said resilient member being in a relaxed position when said rigid member is in the first position, and a second position in which the catch thereof does not engage the printing machine, said resilient member being in a restrained position when said rigid member is in the second position, said handle pivoting with said rigid member to release the catch from engagement with the printing machine to release the customer replaceable unit.

12. A printing machine according to claim 11, wherein said resilient member comprises a leaf spring.

13. A printing machine according to claim 11, wherein said rigid member comprises a pin intermediate the catch and the handle for pivotably attaching said rigid member to the customer replaceable unit.

14. A printing machine according to claim 11, wherein the catch comprises a wedge shaped lip.

15. A printing machine according to claim 12, wherein said leaf spring has one end thereof attached to said rigid member intermediate the catch and the handle with the other end thereof being free.

* * * * *